(12) United States Patent
Mishima et al.

(10) Patent No.: US 6,197,012 B1
(45) Date of Patent: Mar. 6, 2001

(54) DISPOSABLE WEARING ARTICLE

(75) Inventors: Yoshitaka Mishima; Tsutomu Kido, both of Mitoyo-gun (JP)

(73) Assignee: Uni-Charm Corporation (JP)

( * ) Notice: Subject to any disclaimer, the term of this patent is extended or adjusted under 35 U.S.C. 154(b) by 0 days.

(21) Appl. No.: 09/202,383
(22) PCT Filed: Apr. 10, 1998
(86) PCT No.: PCT/JP98/01674
  § 371 Date: Dec. 11, 1998
  § 102(e) Date: Dec. 11, 1998
(87) PCT Pub. No.: WO98/46180
  PCT Pub. Date: Oct. 22, 1998

(30) Foreign Application Priority Data

Apr. 11, 1997 (JP) .................................................. 9-093606

(51) Int. Cl.⁷ .................................................. A61F 13/15
(52) U.S. Cl. .................................................. 604/385.04
(58) Field of Search .................. 604/385.01, 385.03, 604/391, 385.04, 358, 385.21, 385.101, 385.22, 385.23

(56) References Cited

U.S. PATENT DOCUMENTS 4,938,753  7/1990  Van Gompel et al. .
5,383,988 *  1/1995  Herrmann et al. ...................... 156/65
5,980,500 * 11/1999  Shimizu et al. ................ 604/358.01

* cited by examiner

Primary Examiner—A. T. Nguyen
(74) Attorney, Agent, or Firm—Baker & Daniels (57) ABSTRACT

Each lateral waist region of a disposable garment in the form of a diaper 1 at least partially 13 comprises a pair of breathable nonwoven fabrics 21, 22 being extendible circumferentially of the diaper but normally under no tension and elastically stretchable hot melt adhesive 23 applied on respective inner surfaces of the nonwoven fabrics 21, 22 so as to extend continuously in the circumferential direction but intermittently in the vertical direction, wherein the adhesive 23 is applied with no tension on the nonwoven fabrics 21, 22.

20 Claims, 6 Drawing Sheets

FIG.8

DISPOSABLE WEARING ARTICLE

FIELD OF THE INVENTION

This invention relates generally to disposable garments such as disposable training pants or disposable shorts for incontinent patients and more particularly to such disposable garments including lateral waist regions being elastic circumferentially of the garments.

BACKGROUND ART

U.S. Pat. No. 4,938,753 discloses a disposable diaper of shorts type provided with side panels which are elastic circumferentially of the diaper. Each of these side panels comprises an elastic woven or nonwoven fabric, a film of elastic material, stretch-bonded laminate which is elastically stretchable and air/liquid-permeable, or the like. "Stretch-bonding" is a technique adopted to bond an elastic member under a tension to a sheet member under no tension. With the laminate obtained by this technique, the sheet member forms gathers as the elastic member contracts after bonded.

With the above-mentioned disposable diaper of prior art, the side panels, i.e., the lateral waist regions may be formed by a breathable woven or nonwoven fabric. However, it is generally difficult to make the lateral waist regions effectively elastic so far as the lateral waist regions are formed by the breathable woven or nonwoven fabric alone. To achieve this, the woven or nonwoven fabric must be made of relatively expensive elastic yarn. Obviously, this is not practical from the viewpoint of a hot competitive pricing in the industry. Certainly, it is possible to provide the lateral waist regions with a high elasticity at a relatively low cost by adopting the well known stretched laminate of woven or nonwoven fabric. However, the diaper obtained in this way will suffer from deterioration of feeling to wear the garment due to many gathers formed in the lateral waist regions which give a wearer uncomfortable rough touch. Additionally, the gathers cause the laminate to be densely folded and consequently deteriorate an expected breathability between in- and exterior of the diaper through the laminate.

SUMMARY OF THE INVENTION

In view of the problem as has been described above, it is an object object of the invention to provide disposable garment having its lateral waist regions improved in elasticity as well as breathability.

According to the invention, there is provided a disposable garment comprising a liquid-permeable topsheet, a liquid-impermeable backsheet and a liquid-absorbent core disposed between these two sheets and having a front waist region, a rear waist region and transversely opposite lateral waist regions extending between the front and rear waist regions, each of the lateral waist regions at least partially comprises breathable nonwoven fabrics being extendible circumferentially of the garment but normally under no tension and a plural lines of elastic material applied on the nonwoven fabrics, the lines of elastic material being elastically stretchable circumferentially of the garment and continuously extending circumferentially of the garment in parallel one to another, wherein the elastic material is applied to the nonwoven fabrics with no tension.

Each of the lateral waist regions can comprise a pair of extendible and breathable nonwoven fabrics placed one upon another and adhesive by means of which respective inner surfaces of the nonwoven fabrics, wherein the elastic material is used as this adhesive.

The elastic material can comprise a residual strain less than 15% as measured after the elastic material has been stretched by 50% and the nonwoven fabrics are extendible in response to the elastic material being stretched.

The nonwoven fabrics can exhibit a residual strain less than 50% as measured after the of nonwoven fabrics have been stretched by 50%.

The elastic material can be applied on the nonwoven fabric so as to define a plurality of stripes extending circumferentially of the garment.

The elastic material can be applied on the nonwoven fabrics so as to define spirals each extending circumferentially of the garment.

The lateral waist regions can comprise wings extending outward from at least one of front and rear waist regions in a disposable diaper of open type.

The lateral waist regions can comprise the corresponding lateral waist regions in a disposable diaper of shorts type.

As will be apparent from the foregoing description, the disposable garment according to the invention includes the lateral waist regions each comprising the extendible and breathable nonwoven fabric applied under no tension with the elastic adhesive material which is also under no tension. Accordingly, the lateral waist regions are stretched as the garment is put on a wearer's body. Consequently, the initial fibers interstices of the nonwoven fabric are enlarged and the breathability of the lateral waist regions are improved as the lateral waist regions are stretched. In addition, no significant gathers are formed even after the lateral waist regions have been released from the stretching force. Thus, any apprehension that a feeling to wear the garment might be deteriorated by the gathers or traces of these gathers which might be left on wearer's skin can be simultaneously eliminated. In this manner, the garment according to the invention is particularly suitable as a diaper for baby having delicate and sensitive skin.

DESCRIPTION OF THE BEST MODE FOR WORKING OF THE INVENTION

Details of a disposable garment according to the invention will be more fully understood from the description of disposable diaper as a specific embodiment of the invention given hereunder with reference to the accompanying drawings.

Figure 1:
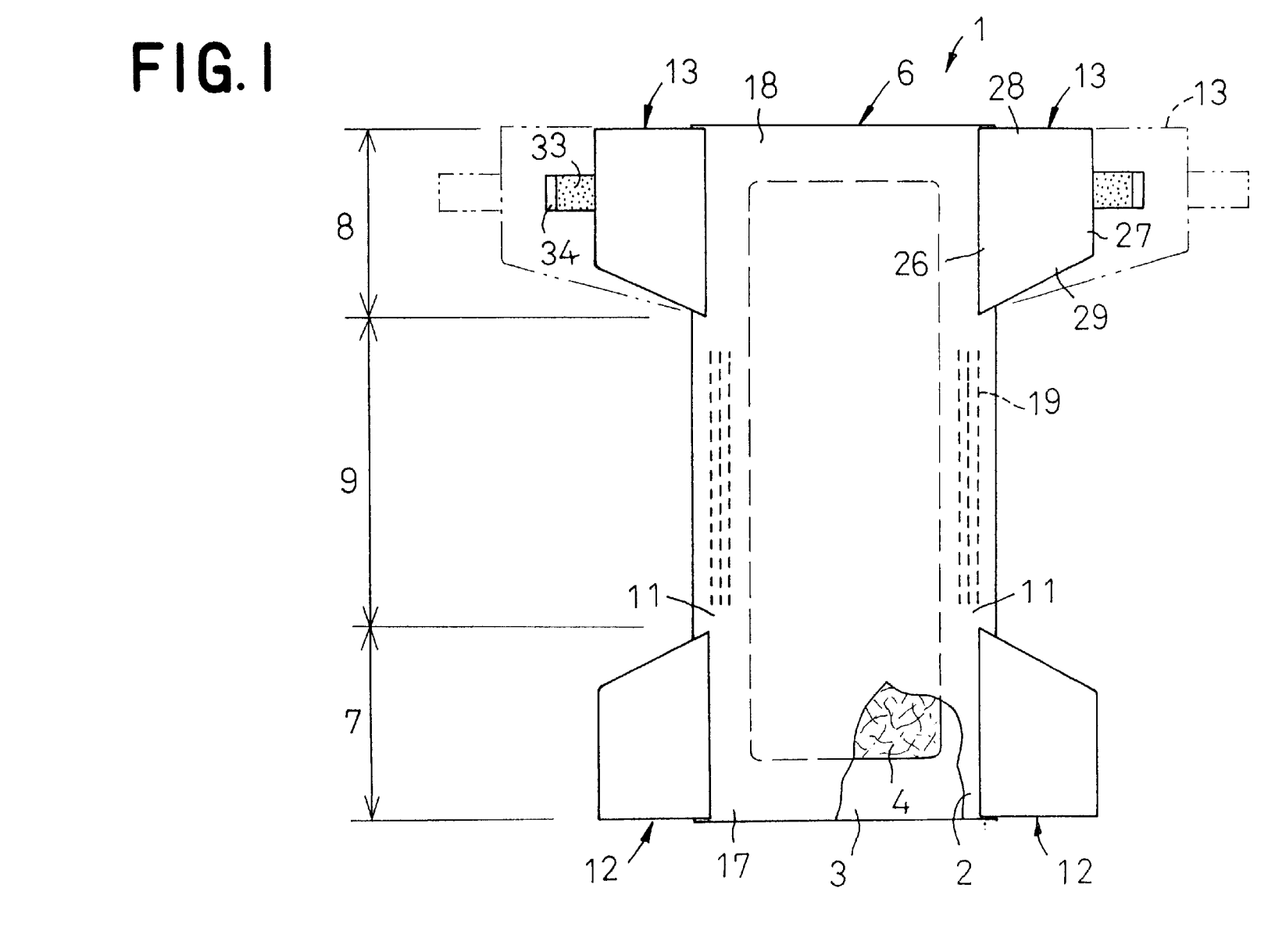
FIG. 1 is a plan view showing a disposable diaper according to the invention as partially broken away.
Figure 2:
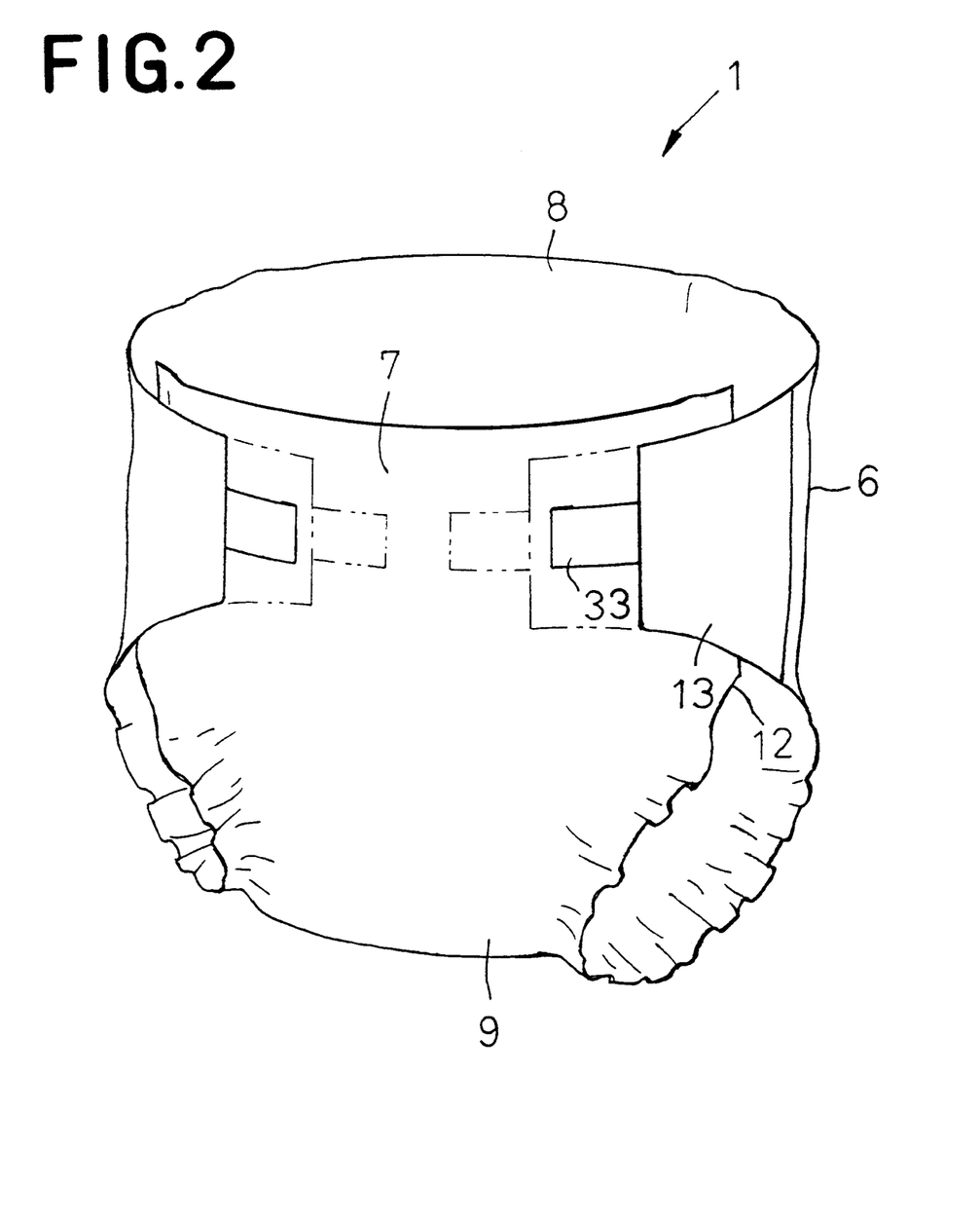
FIG. 2 is a perspective view showing the diaper in its state put on a wearer's body.

FIGS. 1 and 2 are respectively a plan view showing an inner side of a disposable diaper 1 as partially broken away and a perspective view showing this diaper in its state put on a wearer's body.

The diaper 1 has a main body 6 comprising a liquid-permeable topsheet 2, a liquid-impermeable backsheet 3 and a liquid-absorbent core 4 disposed between these two sheets 2, 3. The main body 6 is defined by a front waist region 7, a rear waist region 8 and a crotch region 9 extending between these two waist regions 7, 8. Each of the front and rear waist regions 7, 8 is provided with a pair of front wings 12 and a pair of rear wings 13 extending outward from transversely opposite sides thereof. These front and rear wings 12, 13 serve to form transversely opposite side regions of the diaper 1 as it is put on a wearer's body. Of the front and rear wings 12, 13, the rear wings 13 are formed so as to be elastic transversely of the main body 6 as indicated by imaginary lines in FIG. 1 (circumferentially of the diaper 1 as viewed in FIG. 2) while the front wings 12 are formed so as to be substantially inelastic transversely of the main body 6.

In the main body 6, the topsheet 2 and the backsheet 3 extend outward beyond a peripheral edge of the longitudinally larger core 4 and are bonded together by means of hot melt adhesive 16 along these extensions to form transversely opposite side flaps 11, 11 and longitudinally opposite end flaps 17, 18. At least in the crotch region 9, the respective side flaps 11, 11 are provided with a plurality of longitudinally extending elastic members 19 associated with respective leg-openings. These elastic members 19 are disposed between the topsheet 2 and the backsheet 3 and bonded under an appropriate tension to an inner surface of the topsheet 2 and/or the backsheet 3.

Figure 3:
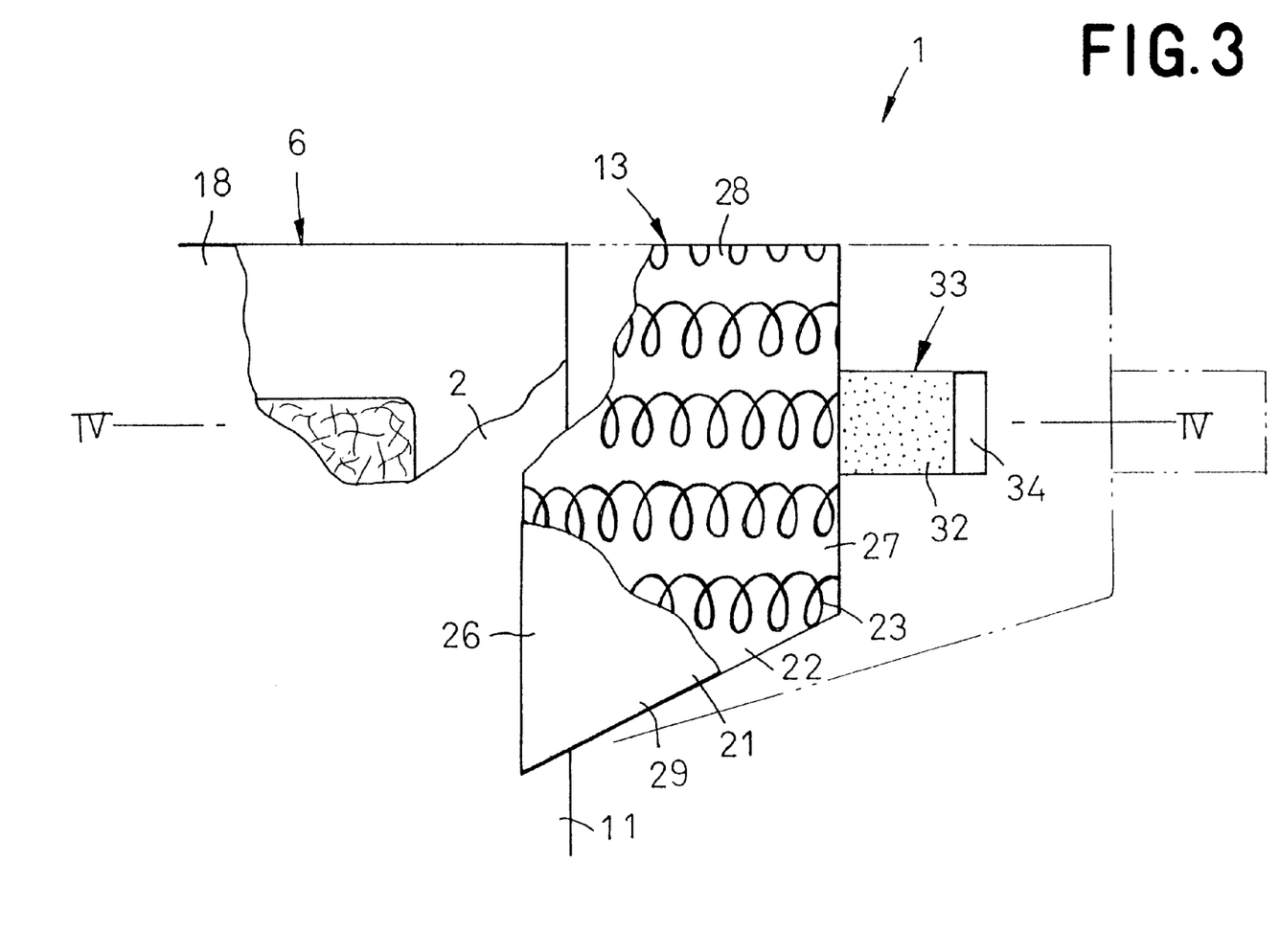
FIG. 3 is a fragmentary plan view showing a part of the diaper as partially broken away.
Figure 4:
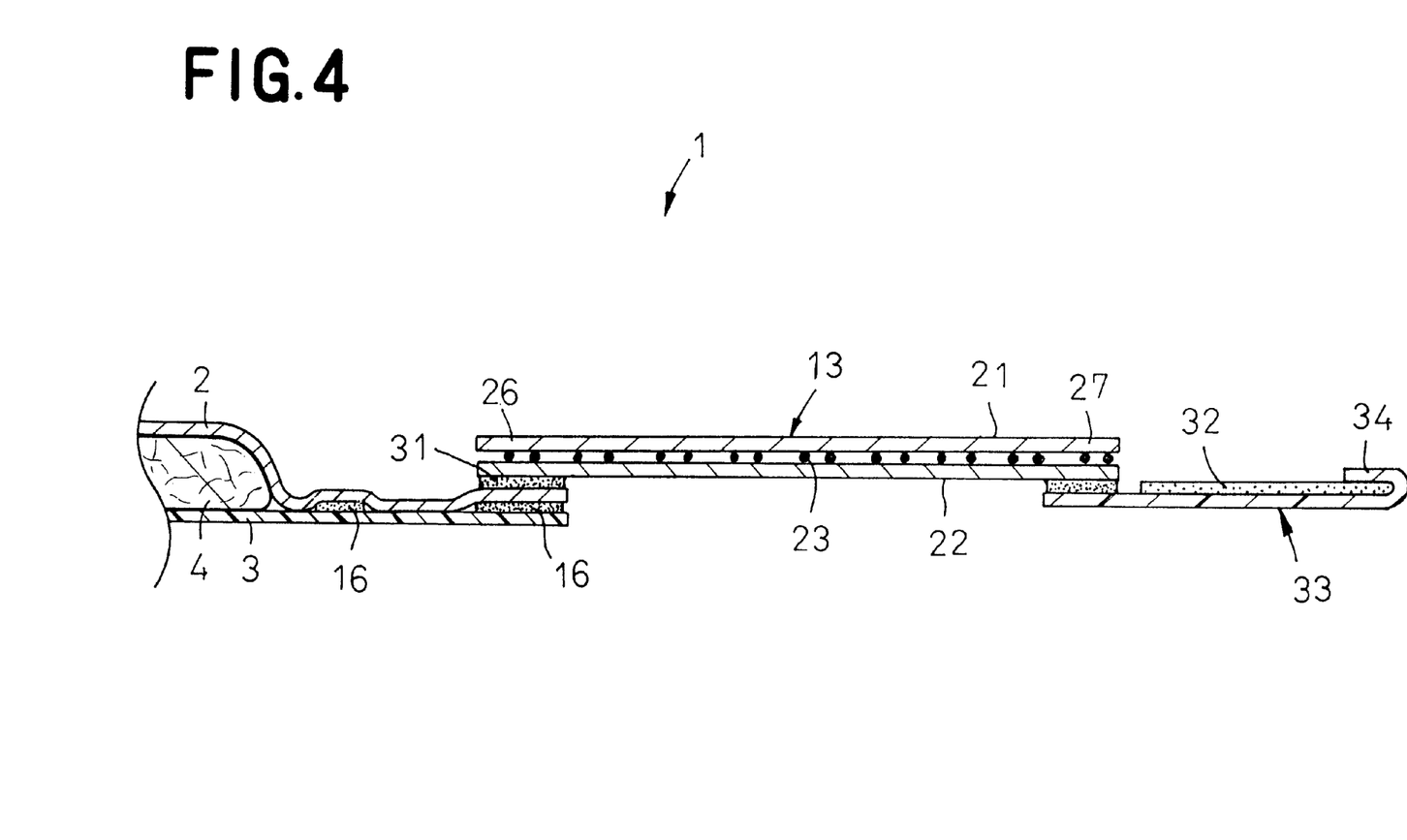
FIG. 4 is a sectional view taken along a line IV—IV in FIG. 3.

FIGS. 3 and 4 are respectively a fragmentary plan view showing a part of the rear waist region 8 as partially broken away and a sectional view taken along a line IV—IV in FIG. 3. Each of the rear wings 13 is made of a laminate which comprises a first sheet 21 defining an inner surface thereof, a second sheet 22 defining an outer surface thereof and adhesive 23 disposed between these first and second sheets 21, 22. The wing 13 is defined by inner and outer side edges 26, 27 in its transversal direction and by upper and lower ends 28, 29 in its longitudinal direction. Along the inner side edge 26, the second sheet 22 is bonded to an outer surface of the topsheet 2 by means of hot melt adhesive 31 along each of the side edges 11 of the main body 6. A tape fastener 33 having its inner surface applied with adhesive 32 extends outward from the outer side edge 27. The tape fastener 33 has its distal end 34 folded back inwardly so as to an inadhesive hold.

In each of the rear wings 13, the first and second sheets 21, 22 are made of an elastic and breathable nonwoven fabric having a basis weight of 20~150 g/m² and exhibiting a residual strain less than 50%, more preferably, less than 35% relative to an amount of extension as measured immediately after these sheets 21, 22 have been released from a force stretching them by 50% transversely of the diaper 1. Such nonwoven fabric may be, for example, of a spun laced or spun bonded nonwoven fabric comprising conjugated fibers exhibiting an elasticity in its crimped state.

Adhesive 23 used to bond these two sheets of nonwoven fabric may be elastically stretchable hot melt adhesive exhibiting a residual strain less than 15%, more preferably, less than 10% relative to an amount of extension as measured immediately after the adhesive 23 has been released from a force stretching it by 50%. Such adhesive 23 is disposed between the first and second sheets 21, 22 so as to describe a plurality of lines which continuously extend in parallel one to another transversely of the diaper 1 and are spaced apart one from another vertically of the diaper 1. For example, such adhesive 23 may be disposed between those two sheets 21, 22 so that each of the lines describes a spiral line extending transversely of the diaper 1 as shown in FIG. 3. An area of the rear wing 13 to be applied with the adhesive 23 is preferably 5~50% relative to the entire area of the wing 13 in order to minimize deterioration of its breathability due to bonding. An example of suitable adhesive 23 is hot melt adhesive obtained by mixing, under heating, block copolymer of 100 parts by weight, adhesive resin such as hydrogenated terpene resin of 20~200 parts by weight and softening agent such as paraffin oil of 5~100 parts by weight. The block copolymer sometimes comprises elastic polymer segment such as butadiene polymer and ethylene/propylene polymer, and polystyrene polymer segment containing polystyrene of 10~60% by weight. With such composition, it is easy for this adhesive to be applied in a linear pattern using a conventional hot melt applicator set to a temperature of approximately 160° C. and a high tackiness is obtained after application of the adhesive.

While the front wings 12 may be formed by the same material as that making up the rear wings 13, it is also possible to form the front wings 12 by a substantially inelastic nonwoven fabric or film alone, or by a laminate of these nonwoven fabric and film. The diaper 1 may have the front wings 12 which are elastically stretchable transversely of the waist regions and the rear wings 13 which are inelastic in any direction. However, from the viewpoint of the usual procedure to put the diaper 1 on a wearer's body, the rear wings 13 are preferably elastic.

To put the disposable diaper 1 designed as has been described above on a wearer's body, the rear wings 13 are stretched toward the front waist region 7 and the tape fasteners 33 are anchored on outer surfaces of the respective front wings 12 or the outer surface of the front waist region 7. The first and second sheets 21, 22 of the rear wings 13 are made of a breathable nonwoven fabric and allow the lateral waist regions of the diaper 1 put on a wearer's body to be maintained breathable. To improve such breathability, the front wings 12 to be placed under the rear wings 13 also are preferably made of a breathable nonwoven fabric. The rear wings 13 additionally contribute to improvement of the breathability in the lateral waist regions since fibrous interstices of the nonwoven fabric making up these rear wings 13 are enlarged as these rear wings 13 are stretched.

The presence of the elastic hot melt adhesive 23 enables the rear wings 13 to be elastically stretched and therefore it is easy to adjust a circumferential fastening force when the tape fasteners 33 are anchored on the front wings 12 or the front waist region 7. The rear wings 13 are elastic but neither have nor generate remarkable gathers as the disposable diaper of prior art has been the case. Accordingly, the rear wings 13 of the invention is free from the problem such that the presence of these gathers deteriorates a feeling to wear the diaper, for example, by giving a wearer's skin an uncomfortable rough touch, or traces of these gathers being left on a wearer's skin. Particularly when the first and second sheets of the rear wings 13 exhibit a residual strain less than 50%, the rear wings 13 are able to adequately contract without formation of remarkable gathers even after they have been stretched to be anchored on and then peeled off from the front waist region for properly wearing. In other words, even after the rear wings 13 have been anchored again on the front waist region 7, there is no apprehension that a feeling to wear the diaper 1 might be thereby deteriorated.

Figures 5, 6:
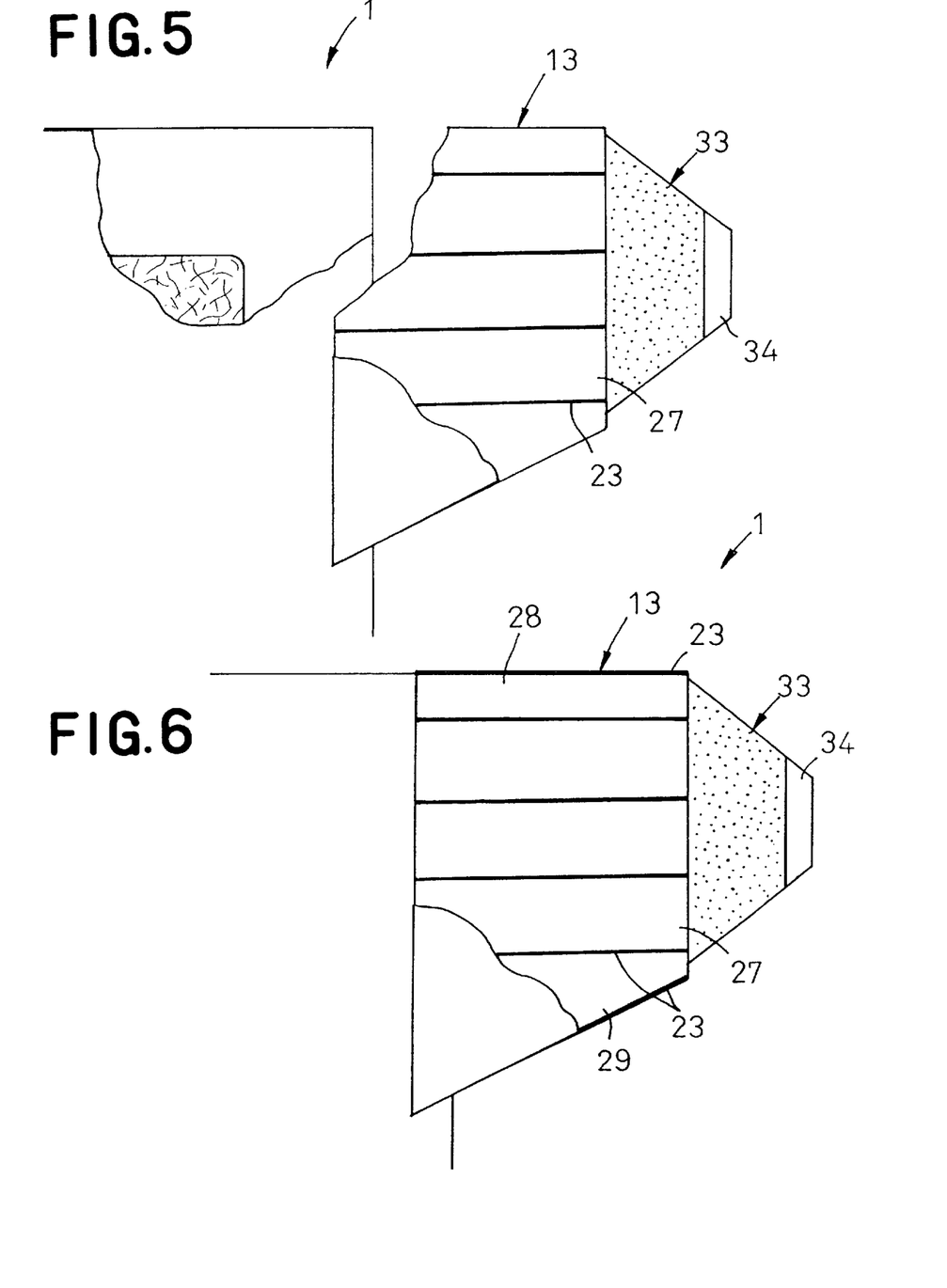
FIG. 5 is a view similar to FIG. 3 showing another embodiment of the invention.
FIG. 6 is a view similar to FIG. 5 showing still another embodiment of the invention.

FIG. 5 is a view similar to FIG. 3 showing another embodiment of the invention. In the rear wings 13 of the diaper 1 according to this embodiment, the elastic hot melt adhesive 23 describes a plurality of rectilinear stripes extending transversely of the diaper 1. The tape fastener 33 of the diaper 1 has its width gradually enlarged from the distal end 34 toward the outer edge 27 of the rear wing 13 so that the rear wing 13 may be stretched substantially over its entire width circumferentially toward the front waist region 7 as the tape fastener 33 is pulled.

FIG. 6 is a view similar to FIG. 5 showing still another embodiment of the invention. In the rear wings 13 of the diaper 1 according to this embodiment, upper and lower edges 28, 29 thereof are also applied with the adhesive 23 so that the wings 13 may be stretched substantially over their entire widths as the wings 13 are pulled.

While the front and rear wings 12, 13 are illustrated to be bonded to the topsheet 2 in these embodiments, it is also possible to bond these wings 12, 13 to the backsheet 3 or to sandwich these wings 12, 13 between the topsheet 2 and the backsheet 3 or even to sandwich the topsheet 2 and the backsheet 3 between the first and second sheets 21, 22 making up the wings 12, 13, respectively. Of the diaper 1, the topsheet 2 may be of a nonwoven fabric containing thermoplastic synthetic fibers of 50% by weight or higher or a porous thermoplastic synthetic resin film. The backsheet 3 may be of a thermoplastic synthetic resin film. Such nonwoven fabric or film may be inelastic or elastic circumferentially of the diaper 1. Bonding of the diaper components may be achieved by heat-sealing the components with each other instead of using the hot melt adhesive so far as the zone in which the components are bonded together requires no elasticity. At least one of the longitudinally opposite end flaps 17, 18 of the diaper 1 may be provided with a circumferentially extendible elastic member bonded thereto under an appropriate tension.

Figure 7:
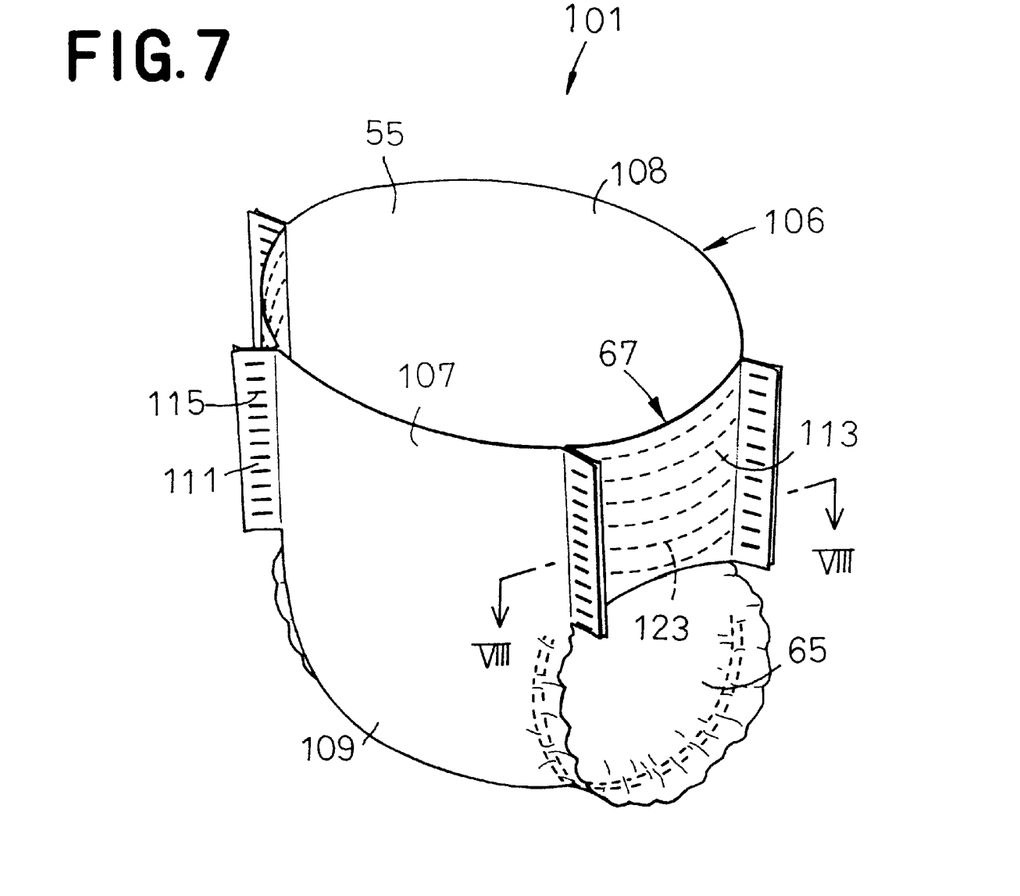
FIG. 7 is a perspective view showing a shorts type disposable diaper according to a further embodiment of the invention.
Figure 8:
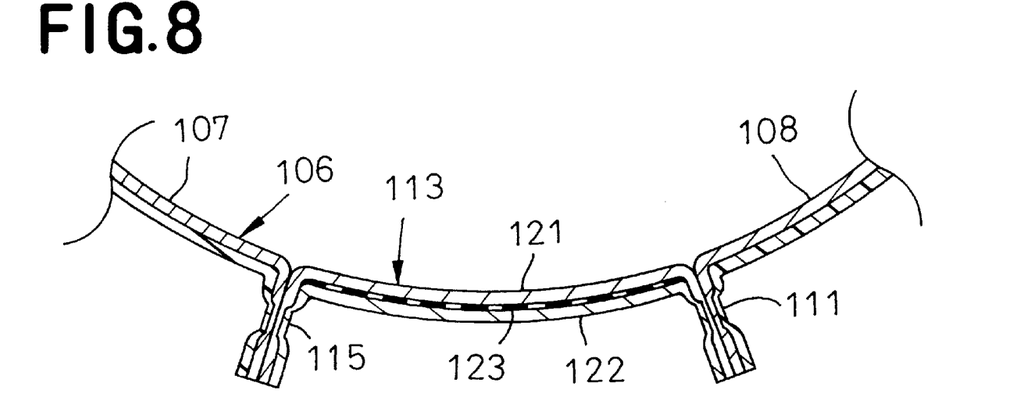
FIG. 8 is a sectional view taken along a line VIII—VIII in FIG. 7.

FIGS. 7 and 8 are respectively a perspective view and a sectional view taken along a line VIII—VIII in FIG. 7 both showing further another embodiment of the invention in the form of shorts type disposable diaper 101. The diaper 101 comprises a main body 106 having of front and rear waist regions 107, 108 and a crotch region 109; and transversely opposite lateral members 113 covering transversely opposite side zones of the waist regions 107, 108. Similarly to the main body 6 in the diaper 1 shown by FIG. 1, the front and rear waist regions 107, 108 of the main body 6 are connected by the lateral members 113 along transversely opposite side edges 111 so as to form a waist-opening 55 and a pair of leg-openings 65.

Each of the lateral members 113 comprises a pair of breathable nonwoven fabric sheets 121, 122 placed one upon another and offering the same effect as the nonwoven fabric sheets 21, 22 and elastically stretchable hot melt adhesive 123 equivalent to the hot melt adhesive 23, i.e., by means of which respective inner surfaces of the pair of nonwoven fabric sheets 121, 122 are bonded together. The lateral member 113 is bonded to the associated side edge 111 of the main body 106 along a heat-sealed zone 115 by ultrasonic treatment. The adhesive 123 having an elasticity circumferentially of the waist regions is applied on the sheets 121, 122, similarly to the adhesive 23 applied to the rear wings 13, so as to describe a plurality of stripes continuously extending in the circumferential direction in parallel one to another. The pair of nonwoven fabric sheets 121, 122 are bonded together with no tension by means of the adhesive 123 which is also under no tension.

It should be understood that the invention is not limited to the disposable diaper 1, 101 as have been described above with reference to the accompanying drawings but can be implemented in the other forms of disposable garments such as disposable training pants and disposable pants for incontinent patients.

The invention can be extensively exploited for garments such as training pants, disposable incontinence pants, disposable diapers for infants and adults, diaper covers or the like.

What is claimed is:

1. A disposable garment comprising:

a liquid-permeable topsheet;

a liquid-impermeable backsheet; and a liquid-absorbent core disposed between the liquid-permeable topsheet and the liquid-impermeable backsheet, the disposable garment having a front waist region, a rear waist region and transversely opposite lateral waist regions extending between the front and rear waist regions, each of the lateral waist regions at least partially comprises a pair of breathable nonwoven fabrics placed one upon another which are extendable circumferentially of the garment when tension is applied thereto and a plurality of line of elastic adhesive material applied between the pairs of nonwoven fabric to bond the same together, the lines of elastic adhesive material being elastically stretchable circumferentially of the garment and continuous in a direction which is circumferential with respect to the garment in parallel one to another, the lines of elastic adhesive material being applied to the nonwoven fabrics when the nonwoven fabrics are not subject to tension.

2. A disposable garment according to claim 1, wherein the elastic adhesive material comprises a hot melt adhesive.

3. A disposable garment according to claim 1, wherein the elastic adhesive material exhibits a residual strain of less than 15% as measured after the elastic adhesive material has been stretched by 50% and the nonwoven fabrics are extendable as the elastic adhesive material is stretched.

4. A disposable garment according to claim 1, wherein the nonwoven fabrics exhibit a residual strain less than 50% as measured after the nonwoven fabrics have been stretched by 50%.

5. A disposable garment according to claim 1, wherein the elastic adhesive material is applied to the nonwoven fabrics as a plurality of stripes extending circumferentially of the garment.

6. A disposable garment according to claim 1, wherein the elastic adhesive material is applied to the nonwoven fabrics in spiral patterns which extend circumferentially of the garment.

7. A disposable garment according to claim 1, wherein the disposable garment comprises an open disposable diaper and the lateral waist regions comprise wings which extend outward from at least one of front and rear waist regions.

8. A disposable garment according to claim 1, wherein the disposable garment comprises a disposable diaper shaped as a pair of shorts.

9. A disposable garment according to claim 2, wherein the elastic adhesive material is applied to the nonwoven fabrics as a plurality of stripes extending circumferentially of the garment.

10. A disposable garment according to claim 2, wherein the elastic adhesive material is applied to the nonwoven fabrics in spiral patterns which extend circumferentially of the garment.

11. A disposable garment according to claim 2, wherein the disposable garment comprises an open disposable diaper and the lateral waist regions comprise wings which extend outward from at least one of front and rear waist regions.

12. A disposable garment according to claim 2, wherein the disposable garment comprises a disposable diaper shaped as a pair of shorts.

13. A disposable garment according to claim 5, wherein the disposable garment comprises an open disposable diaper and the lateral waist regions comprise wings which extend outward from at least one of front and rear waist regions.

14. A disposable garment according to claim 5, wherein the disposable garment comprises a disposable diaper shaped as a pair of shorts.

15. A disposable garment according to claim 6, wherein the disposable garment comprises an open disposable diaper and the lateral waist regions comprise wings which extend outward from at least one of front and rear waist regions.

16. A disposable garment according to claim 6, wherein the disposable garment comprises a disposable diaper shaped as a pair of shorts.

17. A disposable garment according to claim 9, wherein the disposable garment comprises an open disposable diaper and the lateral waist regions comprise wings which extend outward from at least one of front and rear waist regions.

18. A disposable garment according to claim 9, wherein the disposable garment comprises a disposable diaper shaped as a pair of shorts.

19. A disposable garment according to claim 10, wherein the disposable garment comprises an open disposable diaper and the lateral waist regions comprise wings which extend outward from at least one of front and rear waist regions.

20. A disposable garment according to claim 10, wherein the disposable garment comprises a disposable diaper shaped as a pair of shorts.

* * * * *